(12) United States Patent
Hatanaka et al.

(10) Patent No.: US 9,308,187 B2
(45) Date of Patent: Apr. 12, 2016

(54) ADHESIVE PATCH COMPRISING DICLOFENAC SODIUM

(71) Applicant: HISAMITSU PHARMACEUTICAL CO., INC., Tosu-shi (JP)

(72) Inventors: Eisuke Hatanaka, Tsukuba (JP); Yasunori Takada, Tsukuba (JP); Takaaki Terahara, Tosu (JP); Naruhito Higo, Tsukuba (JP)

(73) Assignee: HISAMITSU PHARMACEUTICAL CO., INC., Tosu-shi (JP)

( * ) Notice: Subject to any disclaimer, the term of this patent is extended or adjusted under 35 U.S.C. 154(b) by 0 days.

(21) Appl. No.: 14/408,482

(22) PCT Filed: Jun. 17, 2013

(86) PCT No.: PCT/JP2013/066574
§ 371 (c)(1),
(2) Date: Mar. 23, 2015

(87) PCT Pub. No.: WO2013/191128
PCT Pub. Date: Dec. 27, 2013

(65) Prior Publication Data
US 2015/0202171 A1 Jul. 23, 2015

(30) Foreign Application Priority Data

Jun. 20, 2012 (JP) .................................. 2012-138802

(51) Int. Cl.
| | | |
|---|---|---|
| *A61K 31/196* | (2006.01) | |
| *A61K 9/70* | (2006.01) | |
| *A61K 9/00* | (2006.01) | |
| *A61K 47/12* | (2006.01) | |
| *A61K 47/20* | (2006.01) | |

(52) U.S. Cl.
CPC ............. *A61K 31/196* (2013.01); *A61K 9/0014* (2013.01); *A61K 9/7038* (2013.01); *A61K 9/7061* (2013.01); *A61K 47/12* (2013.01); *A61K 47/20* (2013.01)

(58) Field of Classification Search
None
See application file for complete search history.

(56) References Cited

U.S. PATENT DOCUMENTS

| | | | | |
|---|---|---|---|---|
| 4,738,848 | A * | 4/1988 | Yoshida et al. | ............... 424/448 |
| 6,262,121 | B1 * | 7/2001 | Kawaji et al. | ................ 514/567 |
| 2003/0175331 | A1 | 9/2003 | Sasaki et al. | |
| 2012/0283671 | A1 * | 11/2012 | Shibata et al. | ............... 604/307 |

FOREIGN PATENT DOCUMENTS

| | | |
|---|---|---|
| CN | 1489996 A | 4/2004 |
| JP | 61-280426 A | 12/1986 |
| JP | 62-181226 A | 8/1987 |
| JP | 8-500365 A | 1/1996 |
| JP | 11-322595 A | 11/1999 |
| JP | 2002-338462 A | 11/2002 |
| JP | 2007-511605 A | 5/2007 |
| WO | WO 2011/083787 A1 | 7/2011 |
| WO | WO 2012/022837 A1 | 2/2012 |

OTHER PUBLICATIONS

International Search Report issued on Sep. 3, 2013 in PCT/JP2013/066574.
International Preliminary Report on Patentability and Written Opinion issued on Dec. 31, 2014 in PCT/JP2013/066574.
Philip Fuller, et al., "Diclofenac sodium topical solution with dimethyl sulfoxide, a viable alternative to oral nonsteroidal anti-inflammatories in osteoarthritis: review of current evidence",, Journal of Multidisciplinary Healthcare, Abstract, vol. 4, 2011, p. 223-231.
Rajesh Dubey, et al., "Ketorolac Tromethamine Transdermal Gel: Development, In Vitro and In Vivo Evaluation", J. Pain Palliat, Care Pharmacother, vol. 23, No. 1, 2009, pp. 26-34.
Office Action issued Feb. 18, 2015 in Japanese Patent Application No. 2014-521452 (with partial English language translation).
Extended European Search Report dated Feb. 3, 2016 in Application No. 13807634.4.

* cited by examiner

*Primary Examiner* — Brian Gulledge
*Assistant Examiner* — Celeste A Roney
(74) *Attorney, Agent, or Firm* — Oblon, McClelland, Maier & Neustadt, L.L.P.

(57) ABSTRACT

A patch comprising a support layer and an adhesive layer, wherein the adhesive layer comprises diclofenac sodium, dimethyl sulfoxide, and citric acid; a mass ratio between the diclofenac sodium and the citric acid (mass of diclofenac sodium:mass of citric acid) is 1:0.15 to 1:0.45; and a mass ratio between the diclofenac sodium and the dimethyl sulfoxide (mass of diclofenac sodium:mass of dimethyl sulfoxide) is 1:0.75 to 1:3.

8 Claims, 8 Drawing Sheets

ADHESIVE PATCH COMPRISING DICLOFENAC SODIUM

TECHNICAL FIELD

The present invention relates to a patch.

BACKGROUND ART

Although diclofenac is an excellent nonsteroidal analgesic anti-inflammatory agent, there is a problem that there are cases where it shows side effects such as gastrointestinal disorders when it is orally administered. For this reason, a variety of topical agents for external use whose effective ingredients are diclofenac have been developed and patches comprising diclofenac sodium have been marketed as drugs for topical analgesic application in Japan.

However, although these patches are characterized by good skin permeability of diclofenac, their application is limited to analgesic, anti-inflammatory use topically. As opposed to conventional preparations for topical application that are commercially available, if it is possible to contain diclofenac at high concentrations stably, to have superior releasability and skin permeability of the drug, and to make the blood concentration of diclofenac in the subjects of administration high at the same levels as those by the aforementioned oral administration or administration with suppositories, effectiveness will possibly be shown against systemic disorders (as analgesic anti-inflammatories, antipyretics or the like). Therefore, the development of such novel patches comprising diclofenac and/or a pharmacologically acceptable salt thereof has been wanted.

In addition, there are many cases where diclofenac comprised in patches that are on the market or are being developed is used in the form of a pharmaceutically acceptable salt, particularly a sodium salt from the standpoints of improving its stability, suppressing reduction in physical properties (intensity, elasticity, durability, adhesiveness, and the like) of the adhesive layers of the patches, decreasing irritation to the skin, etc. However, diclofenac sodium is scarcely soluble in ether but is relatively soluble in water; since its percutaneous absorbability is insufficient, a variety of measures have been taken.

For example, in Japanese Unexamined Patent Application No. Sho 61-280426 (Patent Literature 1), there is described that by using an organic acid such as citric acid in combination with diclofenac sodium to have them comprised in the pressure-sensitive adhesive material layer of an analgesic anti-inflammatory patch, the solubility and skin permeability of diclofenac sodium in the patch are improved. Also, in Japanese Unexamined Patent Application No. Sho 62-181226 (Patent Literature 2), there is described that by using a glycol in addition to an organic acid such as citric acid in combination with diclofenac sodium to have them comprised in the base of an analgesic anti-inflammatory patch, the solubility and skin permeability of diclofenac sodium in the patch are improved. Further, in Japanese Unexamined Patent Application No. 2002-338462 (Patent Literature 3), there is described that by combining and compounding diclofenac sodium, an organic acid such as citric acid, pyrrolidone or a derivative thereof, and an aliphatic acid ester of polyvalent alcohol in the base of an adhesive poultice, diclofenac sodium is stably solubilized in the base to improve the releasability from the poultice and the percutaneous absorbability.

CITATION LIST

Patent Literature

[PTL 1] Japanese Unexamined Patent Application No. Sho 61-280426
[PTL 2] Japanese Unexamined Patent Application No. Sho 62-181226
[PTL 3] Japanese Unexamined Patent Application No. 2002-338462

SUMMARY OF INVENTION

Technical Problem

As described above, the skin permeability or the like of diclofenac sodium in patches will be improved by virtue of the addition of organic acids such as citric acid. However, as a result of the studies by the present inventors, it has become clear that by simply compounding diclofenac sodium and citric acid, the time-dependent crystallization of diclofenac or diclofenac sodium results in the adhesive layers of patches, as will be shown in the Examples to be mentioned later. Therefore, since the time-dependent crystallization of diclofenac or diclofenac sodium results in the analgesic anti-inflammatory patches as described in Patent Literatures 1-3, these analgesic anti-inflammatory patches are not sufficient from the standpoint that diclofenac sodium is comprised stably in the adhesive layers at high concentrations; consequently, their effectiveness against systemic symptoms (as analgesic anti-inflammatory, antipyretics or the like) by the percutaneous administration of diclofenac has not been expected.

The present invention has been made in view of the above-described problems of the prior art and an object of the present invention is to provide a patch where the crystallization of diclofenac and diclofenac sodium is suppressed and which is excellent in the skin permeability of diclofenac.

Solution to Problem

The present inventors have conducted earnest studies to achieve the above-described object, and consequently have revealed that among a variety of solubilizers, dimethyl sulfoxide, N-methylpyrrolidone, polyethylene glycol, and dipropylene glycol are excellent in the solubilizing power for diclofenac sodium and diclofenac. Especially, they have found that when a styrene-isoprene-styrene block copolymer is used as the adhesive layer of a patch, dimethyl sulfoxide displays excellent skin permeability even for diclofenac sodium with low skin permeability.

However, when dimethyl sulfoxide was added in the adhesive layer, the solubility of diclofenac sodium during an initial period of production was good but crystals formed in a time-dependent manner. Similarly to citric acid as mentioned above, dimethyl sulfoxide alone was unsuitable for use in patches as the solubilizer of diclofenac sodium.

However, the present inventors have conducted further earnest studies to achieve the above-described object, and consequently have found that when diclofenac sodium is comprised in the adhesive layer of a patch, the crystallization of diclofenac and diclofenac sodium can be suppressed by using dimethyl sulfoxide as a solubilizer and further by including citric acid at a predetermined mass ratio relative to diclofenac sodium. The present inventors have also revealed that the patch provided with an adhesive layer comprising diclofenac sodium, dimethyl sulfoxide, and citric acid at a predetermined mass ratio has also excellent skin permeability as compared with conventional patches comprising citric acid and diclofenac sodium. Moreover, the present inventors have additionally found that the patch which uses dimethyl sulfoxide as the solubilizer has strong irritation to the skin but that this irritation is reduced by the combined use of citric acid and have completed the present invention.

Specifically, the patch of the present invention is a patch comprising a support layer and an adhesive layer, wherein the adhesive layer comprises diclofenac sodium, dimethyl sulfoxide, and citric acid; a mass ratio between the diclofenac sodium and the citric acid (mass of diclofenac sodium:mass of citric acid) is 1:0.15 to 1:0.45; and a mass ratio between the diclofenac sodium and the dimethyl sulfoxide (mass of diclofenac sodium:mass of dimethyl sulfoxide) is 1:0.75 to 1:3.

Further, it is preferred that for the adhesive layer according to the present invention, a mass ratio between the diclofenac sodium and the dimethyl sulfoxide is 1:0.75 to 1:2. Furthermore, the adhesive layer preferably further comprises oleic acid.

Advantageous Effects of Invention

According to the present invention, it will be possible to provide a patch where the crystallization of diclofenac and diclofenac sodium is suppressed, skin irritation is less, and the skin permeability of diclofenac is excellent.

DESCRIPTION OF EMBODIMENTS

Hereinafter, the present invention will be described in detail based on preferred embodiments thereof.

A patch of the present invention comprises a support layer and an adhesive layer formed on surface(s) (normally onto one surface) of the support layer and comprises diclofenac sodium, dimethyl sulfoxide, and citric acid in the adhesive layer.

First, the adhesive layer according to the present invention will be described. The adhesive layer which is used in the present invention is normally formed onto one surface of the support layer and allows for its attachment to the skin, and it is a layer comprising an adhesive having pressure-sensitive adhesiveness and diclofenac sodium to be absorbed percutaneously.

Diclofenac sodium according to the present invention is a nonsteroidal type drug having analgesic, anti-inflammatory action and is a compound which is also referred to as sodium 2-[2,6-dichlorophenyl]amino]phenyl acetate.

In the patch of the present invention, a content of the thus-mentioned diclofenac sodium can be adjusted, as appropriate, depending on the purpose of therapy. However, it is generally 1 to 20% by mass relative to the total mass of the adhesive layer: it is preferably 2 to 10% by mass from the standpoints that the therapeutic effect easily manifests and that preferable adhesive properties are easily obtainable.

Since the patch of the present invention comprises dimethyl sulfoxide and citric acid in the adhesive layer, it suppresses the crystallization of diclofenac and diclofenac sodium and can stably comprise diclofenac sodium at a high concentration (3% by mass or greater relative to the total mass of the adhesive layer). Further, since the drug releasabilty (water releasability) from the adhesive layer is high, the patch of the present invention can exert the excellent skin permeability of diclofenac. Also, since the patch of the present invention comprises dimethyl sulfoxide and citric acid in the adhesive layer, it can reduce irritation to the skin.

A content of the dimethyl sulfoxide is preferably 1 to 15% by mass, and more preferably, 3 to 10% by mass relative to the total mass of the adhesive layer. If the content of the dimethyl sulfoxide is less than the lower limit, crystals of diclofenac or diclofenac sodium tend to easily precipitate. On the other hand, if it exceeds the upper limit, the adhesive force or cohesion of the adhesive layer tend to lower.

The citric acid according to the present invention may be citric acid anhydride, citric acid hydrate, or in the form of a citrate (such as sodium citrate, potassium citrate, magnesium citrate, or calcium citrate). A content of such citric acid is preferably 0.15 to 9% by mass, and more preferably, 0.25 to 5% by mass relative to the total mass of the adhesive layer. If the content of the citric acid is less than the lower limit, the crystals of diclofenac or diclofenac sodium tend to easily precipitate, while irritation to the skin tends to be higher. On the other hand, if it exceeds the upper limit, the crystals of diclofenac or diclofenac sodium tend to precipitate, while the content of diclofenac sodium tends to lower over time.

Further, in the adhesive layer according the present invention, a mass ratio between diclofenac sodium and the citric acid (mass of diclofenac sodium:mass of citric acid) is required to be 1:0.15 to 1:0.45, and is preferably, 1:0.15 to 1:0.30; a molar ratio between the diclofenac sodium and the citric acid is required to be 1:0.25 to 1:0.75. If the ratio of the mass of the citric acid to the mass of the diclofenac sodium is less than the lower limit, the crystals of diclofenac or diclofenac sodium tend to precipitate, while the therapeutically effective skin permeability of diclofenac tends to be unlikely obtained. On the other hand, even if it exceeds the upper limit, the crystals of diclofenac or diclofenac sodium tend to precipitate.

In addition, in the adhesive layer according the present invention, a mass ratio between the diclofenac sodium and the dimethyl sulfoxide (mass of diclofenac sodium:mass of dimethyl sulfoxide) is required to be 1:0.75 to 1:3 and is preferably 1:0.75 to 1:2. If the ratio of the mass of the dimethyl sulfoxide to the mass of the diclofenac sodium is less than the lower limit, the drug releasabilty (water releasability) of the adhesive layer tends to lower, while the crystals of diclofenac or diclofenac sodium tend to easily precipitate. On the other hand, if it exceeds the upper limit, sufficient adhesive force to the skin or the like tends to be unlikely obtained.

Moreover, in the adhesive layer according the present invention, a total content of the citric acid and the dimethyl sulfoxide can be adjusted, as appropriate, depending on the amount of the diclofenac sodium. However, it is preferably 0.5 to 20% by mass, and more preferably, 1 to 15% by mass relative the total mass of the adhesive layer. If the total content is less than the lower limit, the skin permeability of diclofenac tends to lower, while the crystals of diclofenac or diclofenac sodium tend to easily precipitate. On the other hand, if it exceeds the upper limit, the adhesive force or cohesion of the adhesive tends to lower.

The adhesive layer according to the present invention further comprises oleic acid preferably from the standpoint of more improving the skin permeability of diclofenac. Also, a content of oleic acid is preferably 1 to 10% by mass relative to the total mass of the adhesive layer. If the total content is less than the lower limit, the skin permeability of diclofenac tends to lower and the therapeutic effect tends to easily lower. On the other hand, if it exceeds the upper limit, the adhesive force or cohesion of the adhesive tends to lower.

In addition, there is no particular limitation to an adhesive that is comprised in the adhesive layer according to the present invention and that has pressure-sensitive cohesiveness. The examples include rubber type adhesives, acrylic type adhesives, polyurethane type adhesives, silicone type adhesives, hydrogels comprised of water-soluble polymers, or mixtures of these. Further, as necessary, a tackifier, a plasticizer, and other additives may be comprised in the adhesive layer.

The thus-mentioned rubber type adhesive is a non-aqueous or anhydrous adhesive composition principally consisting of a natural rubber and/or synthetic rubber. Examples of such synthetic rubber include polyisoprene, polyisobutylene, polybutadiene, styrene-butadiene-styrene block copolymers, styrene-isoprene-styrene block copolymers, styrene-butadiene rubbers, and styrene-isoprene rubbers. One of these may be used alone, or a plurality of these may be used in combination. Out of these, from the standpoints that the skin permeability of diclofenac is enhanced and that the cohesion of the patch of the present invention is also enhanced, the styrene-isoprene-styrene block copolymers and/or polyisobutyrene is preferable.

Also, a total content of the natural rubber and/or the synthetic rubber is preferably 10 to 40% by mass, and more preferably, 15 to 35% by mass by mass relative the total mass of the adhesive layer. If the total content is less than the lower limit, the cohesion of the adhesive tends to lower and adhesive remnants tend to increase. On the other hand, if it exceeds the upper limit, the cohesion of the adhesive tends to increase and the adhesive force tends to lower, and in addition, the productivity of the patch tends to lower.

In addition, as the thus-mentioned acrylic type adhesive, there are, for example, mentioned adhesives obtained by polymerizing or copolymerizing at least one member of (meth)acrylic acid, 2-ethylhexyl (meth)acrylate, methyl (meth)acrylate, butyl (meth)acrylate, hydroxyethyl (meth) acrylate, and the like. Further, as the thus-mentioned polyurethane type adhesive, there can be used an aliphatic type polyurethane adhesive or an aromatic type polyurethane adhesive, for example. Additionally, as the thus-mentioned silicone type adhesive, there can be used that which principally consists of a silicone rubber such as polydimethylsiloxane, polymethylvinylsiloxane, or polymethylphenylsiloxane, for example. Moreover, as the thus-mentioned hydrogel consisting of a water-soluble polymer, there can be used that which principally consists of gelatin, cargeenan, hydroxyethylcellulose or the like.

Also, examples of the tackifier include rosin esters, hydrogenated rosin esters, maleated rosins, alicyclic saturated hydrocarbon resins, and terpene resins. Among these, alicyclic saturated hydrocarbon resins, hydrogenated rosin esters, and terpene resins are preferable from the standpoints that the skin permeability of diclofenac is high, irritation to the skin is low, and preferable adhesion properties are also easily obtainable. Furthermore, as the tackifier, there are mentioned ESTER GUM A, AA-G, H, or HP (trade names; Arakawa Chemical Industries, Ltd.), HARIESTER-L, S, or P (trade names; Arakawa Chemical Industries, Ltd.), PINECRYSTAL KE-100 (trade name; Arakawa Chemical Industries, Ltd.), KE-311 (trade name; Arakawa Chemical Industries, Ltd.), HERCOLYN D (trade name; Riken Hercules K. K.), FORAL 85 or 105 (trade name; Riken Hercules K. K.), STEBELITE ESTER 7 or 10 (trade name; Riken Hercules K. K.), PENTALYN 4820 or 4740 (trade name; Riken Hercules K. K.), ARKON P-85 or P-100 (trade names; Arakawa Chemical Industries, Ltd.), and YS RESIN (trade name; Yasuhara Chemical Co. Ltd.). In addition, one kind of such tackifiers may be used alone, or two or more kinds may be used in combination.

Further, a total content of the tackifier is preferably 5 to 60% by mass, and more preferably, 10 to 50% by mass relative the total mass of the adhesive layer. If the total content is less than the lower limit, the adhesive force and the attachability to the skin for a prolonged period tend to lower. On the other hand, if it exceeds the upper limit, the percutaneous absorbability of diclofenac and the shape-holding property tend to lower, and in addition, the pain upon peeling off a patch, skin rash, stickiness and the like tend to increase.

Also, as the plasticizer, there are mentioned petroleum-based oils (such as paraffin-based processed oils, naphthene-based processed oils or aromatic-based process oils), squalane, squalene, vegetable-based oils (such as almond oil, olive oil, camellia oil, castor oil, tall oil, and peanut oil), dibasic acid esters (such as dibutyl phthalate and dioctyl phthalate), and liquid rubbers (such as liquid polybutene and liquid isoprene). One kind of these may be used alone, or two or more kinds may be used in combination. In addition, as the plasticizer, liquid paraffin and liquid polybutene are preferable from the standpoint that the attachability to the skin tends to improve more.

Furthermore, a total content of the plasticizer is preferably 7 to 70% by mass, and more preferably, 10 to 60% by mass relative the total mass of the adhesive layer. If the total content is less than the lower limit, the adhesive force, the percutaneous absorbability of diclofenac, and the dispersability of diclofenac sodium tend to lower. On the other hand, if it exceeds the upper limit, the cohesion and the shape-holding property tend to be lowered, and the pain upon peeling off a patch, stickiness and the like tend to increase.

The adhesive layer according to the present invention can be, as necessary, further contained with an antioxidant (such as ascorbic acid, propyl gallate, butylhydroxyanisole, dibutylhydroxytoluene (BHT), nor-dihydroguaiaretic acid, tocopherol, and tocopherol acetate), an ultraviolet absorber (such as p-aminobenzoic acid, a p-aminobenzoate, amyl p-dimethylaminobenzoate, a salicylate, methyl anthranilate, umbelliferon, esculin, benzyl cinnamate, cinoxate, guaiazulene, urocanic acid, 2-(2-hydroxy-5-methylphenyl)benzotriazole, 4-methoxybenzophenone, 2-hydroxy-4-methoxybenzophenone, octabenzone, dioxybenzone, dihydroxydimethoxybenzophenone, sulisobenzone, benzoresorcinol, octyldimethyl p-aminobenzoate, and ethylhexyl p-methoxycinamate), an antibacterial agent (such as p-hydroxybenzoate, benzoic acid, benzoate, sorbic acid, sorbate, dehydroacetate, 4-isopropyl-3-methylphenol, 2-isopropyl-5-methylphenol, hinokitiol, cresol, 2,4,4-trichloro-2'-hydroxydipheneyl ether, 3,4,4'-trichlorocarbanide, and chlorobutanol), a filler (such as aluminum hydroxide, aluminum silicate hydrate, kaolin, titanium oxide, talc, zinc oxide, silica hydrate, magnesium carbonate, calcium hydrogen phosphate, magnesium silicate, diatomaceous earth, silicic acid anhydrate, bentonite, sodium stearate, calcium stearate, potassium stearate, magnesium stearate, and zinc stearate), a refreshing agent, a perfume, etc.

The adhesive layer according to the present invention is a layer comprising the above-described components and may be a single layer having a single composition or a multilayer in which a plurality of layers having different compositions are laminated. A thickness of such adhesive layer is normally 10 to 500 µm, and preferably, 30 to 300 µm from the standpoint that preferable attachability to the skin and good production suitability are easily obtainable.

Next, a support layer according to the present invention will be described. The support layer to be used in the present invention is to retain the above-described adhesive layer. There can be used a film, a sheet, a sheet-like porous product, a sheet-like foaming product, a fabric, a woven fabric, a nonwoven fabric made of a synthetic resin, including polyethylene, polypropylene, polybutadiene, an ethylene-vinyl acetate copolymer, a vinyl acetate-vinyl chloride copolymer, polyvinyl chloride, a polyamide, a polyester, nylon, a cellulose derivative, and a polyurethane, as well as paper or a laminate of the foregoing. Out of these, from the standpoint that the attachability of a patch to the skin is more easily secured, one having elasticity such as a woven fabric is preferable; from the standpoint of easy handling of the patch, one having self-supportability (such as a film or a sheet-like forming product) is preferable. A thickness of such support layer is preferably 10 to 1500 µm.

Thus far, preferred embodiments of the adhesive layer and the support layer that the patch of the present invention comprises have been described. The patch of the present invention may further comprise a release liner layer for covering and protecting a surface of the adhesive layer until the patch is used. A material of the release liner layer is not particularly limited, but it is preferable to use a sheet material made of a polyester, polypropylene, polyethylene, paper, or a laminate of the foregoing, which has been subjected to releasability treatment (e.g., silicone treatment). In addition, a thickness of such release liner layer is preferably 25 to 150 µm.

Furthermore, an area of the patch of the present invention can be usually set within any range of 1 to 1000 $cm^2$ and is not particularly limited as long as a skin permeation amount of diclofenac that is therapeutically effective can be attained. However, an area of 50 to 200 $cm^2$ is preferable from the standpoint that the adhesive force which is sufficient to make attachment easy and which does not allow for being peeled during the attachment is secured.

In addition, the patch of the present invention can suppress the crystallization of diclofenac and diclofenac sodium and can stably comprise diclofenac sodium at a high concentration (3% by mass or greater relative to the total mass of the adhesive layer). Furthermore, since the drug releasability (water releasability) from the adhesive layer is high, the patch of the present invention allows a larger amount of diclofenac to be percutaneously absorbed than do the already existing patches. Specifically, as will be shown in the Examples to be mentioned later, a large amount of diclofenac at 50 µg/$cm^2$ or more (blood concentration) as a cumulative permeation amount that is equivalent to 24 hours' portion from the start of measurement can be administered to the body in a human skin permeability test.

The patch of the present invention can be produced by employing, as appropriate, a known method for producing a patch, without any particular limitation. For example, various components other than diclofenac sodium that compose the adhesive layer are first mixed at their predetermined proportions at heating under an inert atmosphere such as nitrogen, and then after diclofenac is added thereto at a predetermined proportion, further stirring is conducted to obtain an uniformly solubilized product. Next, the thus-obtained solubilized product is directly applied onto surface(s) of a support layer (normally onto one surface) at a predetermined thickness following an ordinary method to form an adhesive layer. Subsequently, after a surface of the adhesive layer that is opposite to the support layer is covered with the release liner layer and is cut into a predetermined shape, whereby the patch of the present invention can be obtained. Alternatively, after the solubilized product is first applied onto one surface of a release liner layer at a predetermined thickness to form an adhesive layer, a support layer is compression-transferred onto a surface of the adhesive layer that is opposite to the release liner layer and is cut into a predetermined shape, whereby the patch of the present invention may be obtained.

Also, the various components and diclofenac sodium may be added to an organic solvent such as hexane, toluene, and ethyl acetate so that their predetermined proportions may be attained, and stirred to obtain a uniform solubilized product (an adhesive layer composition). Then, this solubilized product is applied onto one surface of a support layer at a predetermined thickness and dried with a dryer or the like, and the organic solvent is removed by evaporation to form an adhesive layer. Subsequently, after a surface of the adhesive layer that is opposite to the support layer is covered with a release liner layer and is cut into a predetermined shape, whereby the patch of the present invention can be obtained. Alternatively, the solubilized product is first applied onto one surface of a release liner layer at a predetermined thickness, dried with a dryer or the like, and the organic solvent is removed by evaporation to form an adhesive layer. Thereafter, a support layer is compression-transferred onto a surface of the adhesive layer that is opposite to the release liner layer and is cut into a predetermined shape, whereby the patch of the present invention may be obtained.

EXAMPLES

Hereinafter, the present invention will be described more specifically based on Examples and Comparative Examples; however, the present invention is not to be limited to the Examples below. Note that an evaluation of crystallization, a skin irritation test, a skin permeation test, a water release test, and an adhesive force test were conducted on patches obtained in the Examples and Comparative Examples, respectively, according to the methods shown below.

(Evaluation of Crystallization)

Each patch was allowed to stand and stored at 60° C. for two weeks. Subsequently, the states of crystals of diclofenac and diclofenac sodium that precipitated on a predetermined area of a surface of the adhesive layer for each patch were observed with the naked eyes or with an optical microscope and were evaluated based on the three-stage indices below representing the states of crystallization.

0: no crystallization on the surface of the adhesive layer
1: observed crystallization scatteredly on the surface of the adhesive layer
2: observed crystallization on the most part of the surface of the adhesive layer (Skin Irritation Test)

A patch which had been cut into a size of 3 cm$^2$ and from which a release liner layer had been removed was attached to the skin of the back part of each 6 subjects (healthy individuals). Then, after a lapse of 24 hours' attachment, the patch was peeled off, and the change of the skin at the site of attachment further after 24 hours was observed visually. Scoring was made by reference to the four-stage indices below, and an average of these scores was determined, whereby the skin irritation of each patch was evaluated.

0: no erythema
1: minimal erythema
2: definite erythema
3: medium to strong erythema (Skin Permutation Test)

Skin on the back of a hairless mouse was peeled off and was mounted to a Franz-type flow-through cell in which hot water at 32° C. was circulated through its outer peripheral part, so that the dermis side of the skin was conformed to the receptor chamber side. Next, a patch which had been cut into a size of 3 cm$^2$ and from which a release liner layer had been removed was attached on the corneum side of this skin. A phosphate buffer solution (pH 7.4) was caused to flow in the receptor chamber of the flow-through cell at a flow rate of 5 mL/hr, and sample liquids were collected from the receptor chamber every 3 to 4 hours for 24 hours' portion from the start of measurement. Each of the collected sample liquids was measured for the concentration of the drug (diclofenac) by high-performance liquid chromatography (HPLC). From the measurement values obtained, the skin permuation amount (F; μg/cm$^2$/hr) of the drug per hour was determined according to the following equation:

$$F\ (\mu g/cm^2/hr) = [\text{drug concentration } (\mu g/ml) \times \text{flow volume (ml)}]/\text{patch area } (cm^2)/\text{time (hr)}$$

The obtained skin permuation amounts of the drug were totaled to determine a cumulative skin permuation amount (μg/cm$^2$) of the drug. Note that it can be understood that a patch with a large value of the cumulative skin permuation amount is excellent in the skin permeability of drug.

A patch which had been cut into a size of 3 cm$^2$ and from which a release liner layer had been removed was attached to the stratum corneum side of a human skin extracted from a dead body and thickness to 500 μm using a dermatome. Then, the cumulative skin permuation amount of each patch for the human skin was determined in a similar manner to the permuation test using the back skin of a hairless mouse.

(Water Release Test)

A test was carried out under the conditions described below in accordance with the water release test using a rotary cylinder as described in the U.S. Pharmacopea Release Test Method. Specifically, a patch which had been cut into a size of 3 cm$^2$ and from which a release liner layer had been removed was fixed to the cylinder at its support layer side with an adhesive. The test was performed under the conditions as follows—test liquid: a phosphate buffer solution (PBS) with pH 7.4; liquid temperature: 32° C.; distance between the lower end of cylinder and the bottom inner face of vessel: 25 mm; number of revolutions: 50 rpm. Sample liquids were collected from the start of test, 1 hour, 3 hours, 6 hours, and 24 hours afterwards, and the amounts of diclofenac released were quantitated by HPLC method and the release rates relative to the theoretical contents were determined as percentages.

(Adhesive Force Test (Peel Test))

A patch which had been cut into a size of 1 cm (wide)×4 cm and from which a release liner layer had been removed was attached to a cleaned Bakelite test board with an adhesive layer of the patch being underside and was pressure-adhered with a roller thereto from over the support layer. About thirty minutes after pressure-adhering, it was set in an Instron type tensile tester (manufactured by A and D Co. Ltd; trade name: "TENSILON"), and the force (gf) required to peel off 180° was measured at 300 mm/min.

Comparative Examples 1 and 2

First, the components listed in Table 1 were weighted out so that they were to be respectively predetermined mass percentages, further mixed after the addition of toluene, and dissolved or dispersed to obtain adhesive layer compositions. Next, they were applied onto one-side surfaces of release liners (PET film treated silicone), and after drying, surfaces that were opposite to the release liners were covered with support layers (PET film) and pressure-adhered, whereby patches were obtained. Further, the obtained patches were evaluated for the crystallization of diclofenac and diclofenac sodium; the results are shown in Table 1 together with the adhesive layer compositions. In addition, the value in a parenthesis represents the mass part of each component of dimethyl sulfoxide, N-methyl-2-pyrrolidone and dipropylene glycol when diclofenac sodium in the adhesive layer of each comparative example was made one mass part.

TABLE 1

| | Comparative Example 1 | Comparative Example 2 |
|---|---|---|
| Diclofenac sodium | 3 (1) | 3 (1) |
| Dimethyl sulfoxide | — | — |
| N-Methyl-2-pyrrolidone | 4 (1.33) | 4 (1.33) |
| Dipropylene glycol | 2 (0.67) | 2 (0.67) |
| Citric acid | 0.9 (0.3) | 1.35 (0.45) |
| Styrene-isoprene-styrene block copolymer | 15 | 15 |
| Polyisobutylene | 5 | 5 |
| Liquid paraffin | 35.1 | 34.65 |
| Alicyclic saturated hydrocarbon resin | 15 | 15 |
| Hydrogenated rosin ester | 15 | 15 |
| Oleic acid | 5 | 5 |
| Crystallization after lapse of 2 weeks at 60° C. | 2 | 2 |

As is evident from the results shown in Table 1, the time-dependent crystallization of diclofenac or diclofenac sodium resulted in the adhesive layer of the patch when diclofenac and citric acid were only compounded. Thus, in order to search for components which suppress the time-dependent crystallization of diclofenac and diclofenac sodium and which can comprise diclofenac sodium in the adhesive layer at a high concentration (3% by mass or greater) of diclofenac, the solubilities of diclofenac and diclofenac sodium were measured in a variety of solubilizers. The obtained results are shown in FIGS. 1 and 2.

Figure 1:
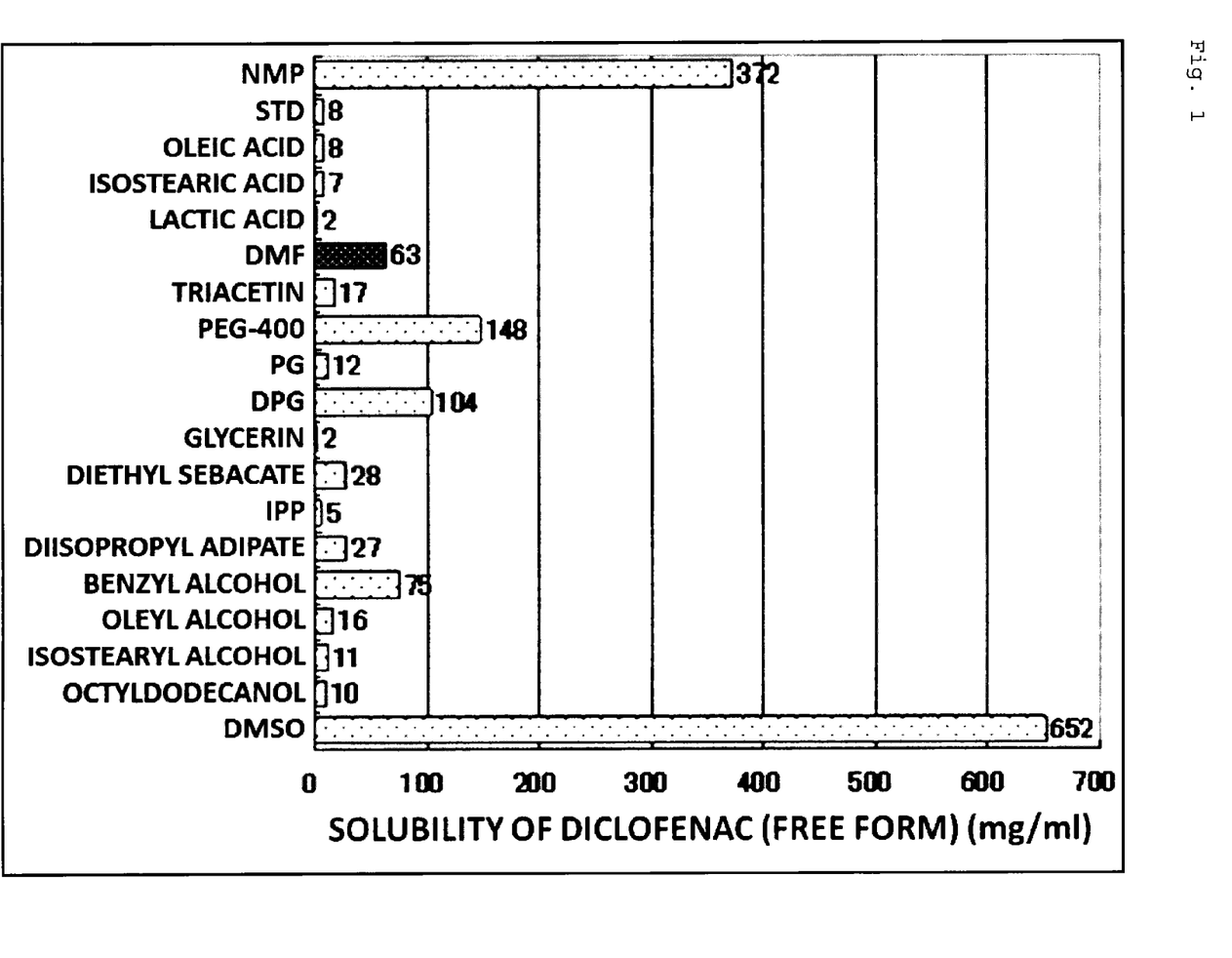
FIG. 1 is a graph showing the solubilities of diclofenac against a variety of solvents.

As is evident from the results shown in FIG. 1, diclofenac was solubilized in dimethyl sulfoxide (DMSO), N-methylpyrrolidone (NMP), polyethylene glycol (PEG-400), and dipropylene glycol (DPG) at high concentrations of 100 mg/ml or greater.

Figure 2:
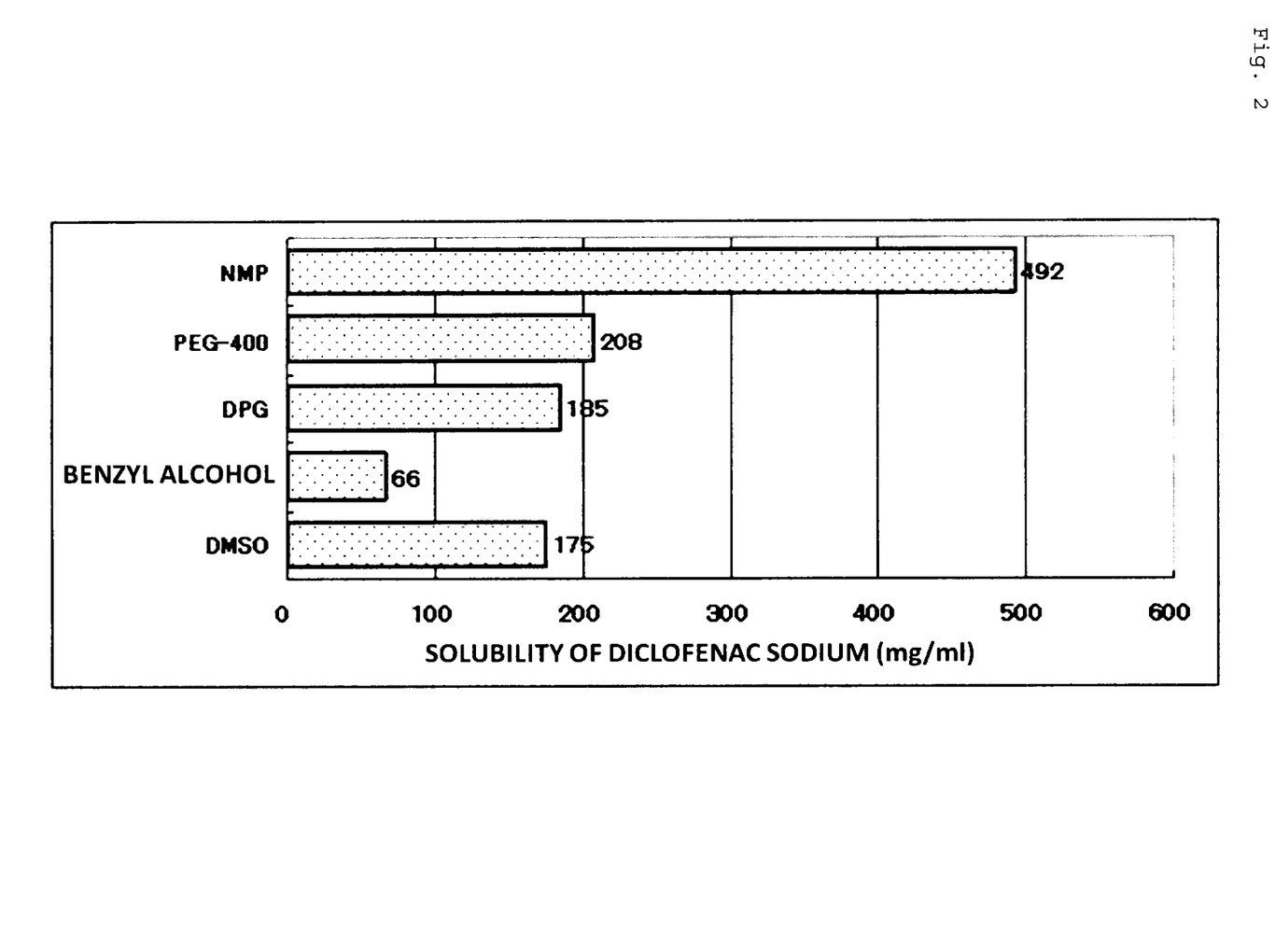
FIG. 2 is a graph showing the solubilities of diclofenac sodium against a variety of solvents.

In addition, as is evident from the results shown in FIG. 2, diclofenac sodium was also solubilized in dimethyl sulfoxide, N-methylpyrrolidone, dipropylene glycol, and polyethylene glycol at high concentrations of 100 mg/ml or greater similarly to diclofenac as its free form.

However, although not shown in the figure, when dimethyl sulfoxide was compounded into the adhesive layer, it was revealed that while the solubility of diclofenac sodium is good at an initial period of production, crystals formed with time and that dimethyl sulfoxide alone was unsuitable for the use as the solubilizer of diclofenac in the patch similarly to citric acid.

Examples 1-4 and Comparative Examples 3 and 4

First, the components listed in Table 2 were weighted out so that they were to be respectively predetermined mass percentages, further mixed after the addition of toluene, and dissolved or dispersed to obtain adhesive layer compositions. Next, they were applied onto one-side surfaces of release liners, and after drying, surfaces that were opposite to the release liners were covered with support layers and pressure-adhered, whereby patches were obtained. Further, the obtained patches were evaluated for the crystallization of diclofenac and diclofenac sodium; the results are shown in Table 2 together with the adhesive layer compositions. In addition, the value in a parenthesis represents the mass part of each component (dimethyl sulfoxide or citric acid) when diclofenac sodium in the adhesive layer of each example or comparative example was made one mass part.

layers comprise diclofenac sodium, dimethyl sulfoxide, and citric acid; a mass ratio of the diclofenac sodium between the citric acid is 1:0.15 to 1:0.45; and a mass ratio between the diclofenac sodium and the dimethyl sulfoxide (mass of diclofenac sodium:mass of dimethyl sulfoxide) is 1:0.75 to 1:3. By contrast, in the patches that did not comprise the adhesive layers according to the present invention (Comparative Examples 3 and 4), the crystals of diclofenac or diclofenac sodium precipitated in a time-dependent manner.

Comparative Examples 5 to 8

First, the components listed in Table 3 were weighted out so that they were to be respectively predetermined mass percentages, further mixed after the addition of toluene, and dissolved or dispersed to obtain adhesive layer compositions. Next, they were applied onto one-side surfaces of release liners, and after drying, surfaces that were opposite to the release liners were covered with support layers and pressure-adhered, whereby patches were obtained. Further, the obtained patches were evaluated for skin irritation; the results are shown in Table 3 together with the adhesive layer compositions. In addition, the value in a parenthesis of table 3 represents the mass part of each component (dimethyl sulfoxide, N-methyl-2-pyrrolidone, dipropylene glycol or citric acid) when diclofenac sodium in the adhesive layer of each example or comparative example was made one mass part.

TABLE 2

|  | Comparative Example 3 | Example 1 | Example 2 | Example 3 | Example 4 | Comparative Example 4 |
|---|---|---|---|---|---|---|
| Diclofenac sodium | 5(1) | 5(1) | 5(1) | 4(1) | 3(1) | 5(1) |
| Dimethyl sulfoxide | 7(1.40) | 7(1.40) | 7(1.40) | 3(0.75) | 5(1.67) | 7(1.40) |
| Citric acid | 0.3(0.06) | 0.75(0.15) | 1.5(0.30) | 1.2(0.3) | 1.35(0.45) | 3(0.60) |
| Styrene-isoprene-styrene block copolymer | 15 | 15 | 15 | 15 | 15 | 15 |
| Polyisobutylene | 5 | 5 | 5 | 5 | 5 | 5 |
| Liquid paraffin | 32.7 | 32.25 | 31.5 | 36.8 | 35.65 | 30 |
| Alicyclic saturated hydrocarbon resin | 15 | 15 | 15 | 15 | 15 | 15 |
| Hydrogenated rosin ester | 15 | 15 | 15 | 15 | 15 | 15 |
| Oleic acid | 5 | 5 | 5 | 5 | 5 | 5 |
| Crystallization after lapse of 2 weeks at 60° C. | 2 | 1 | 0 | 0 | 1 | 2 |

As is evident from the results shown in Table 2, the crystallization of diclofenac and diclofenac sodium was suppressed in the patches of the present invention, which in other words are patches (Examples 1 to 4) wherein the adhesive

TABLE 3

|  | Comparative Example 5 | Comparative Example 6 | Comparative Example 7 | Comparative Example 8 | Example 2 | Example 3 |
|---|---|---|---|---|---|---|
| Diclofenac sodium | — | 5(1) | 3(1) | 5(1) | 5(1) | 4(1) |
| Diclofenac | 2.79 | — | — | — | — | — |
| Dimethyl sulfoxide | 5 | 7(1.40) | 5(1.67) | — | 7(1.40) | 3(0.75) |
| N-Methyl-2-pyrrolidone | — | — | — | 4(0.80) | — | — |
| Dipropylene glycol | — | — | — | 3(0.60) | — | — |
| Citric acid | — | — | — | — | 1.5(0.30) | 1.2(0.3) |
| Mesyl acid | — | 0.75(0.15) | — | — | — | — |

TABLE 3-continued

|  | Comparative Example 5 | Comparative Example 6 | Comparative Example 7 | Comparative Example 8 | Example 2 | Example 3 |
|---|---|---|---|---|---|---|
| Ammonium chloride | — | — | 0.25(0.08) | — | — | — |
| Styrene-isoprene-styrene block copolymer | 15 | 15 | 15 | 15 | 15 | 15 |
| Polyisobutylene | 5 | 5 | 5 | 5 | 5 | 5 |
| Liquid paraffin | 37.21 | 32.25 | 36.75 | 33 | 31.5 | 36.8 |
| Alicyclic saturated hydrocarbon resin | 15 | 15 | 15 | 15 | 15 | 15 |
| Hydrogenated rosin ester | 15 | 15 | 15 | 15 | 15 | 15 |
| Oleic acid | 5 | 5 | 5 | 5 | 5 | 5 |
| Skin irritation score | 0.1 | 2 | 1 | 2 | 0 | 0 |

As is evident from the results shown in Table 3, the skin irritabilities were not observed in the patches of the present invention, which in other words are patches (Examples 2 and 3) wherein the adhesive layers comprise diclofenac sodium, dimethyl sulfoxide, and citric acid; a mass ratio between the diclofenac sodium and the citric acid is 1:0.15 to 1:0.45; and a mass ratio between the diclofenac sodium and the dimethyl sulfoxide (mass of diclofenac sodium:mass of dimethyl sulfoxide) is 1:0.75 to 1:3. By contrast, in the patches that did not comprise the adhesive layers comprising dimethyl sulfoxide as well as comprising mesyl acid or ammonium chloride in place of citric acid (Comparative Examples 6 and 7), strong skin irritations were observed.

Figure 3:
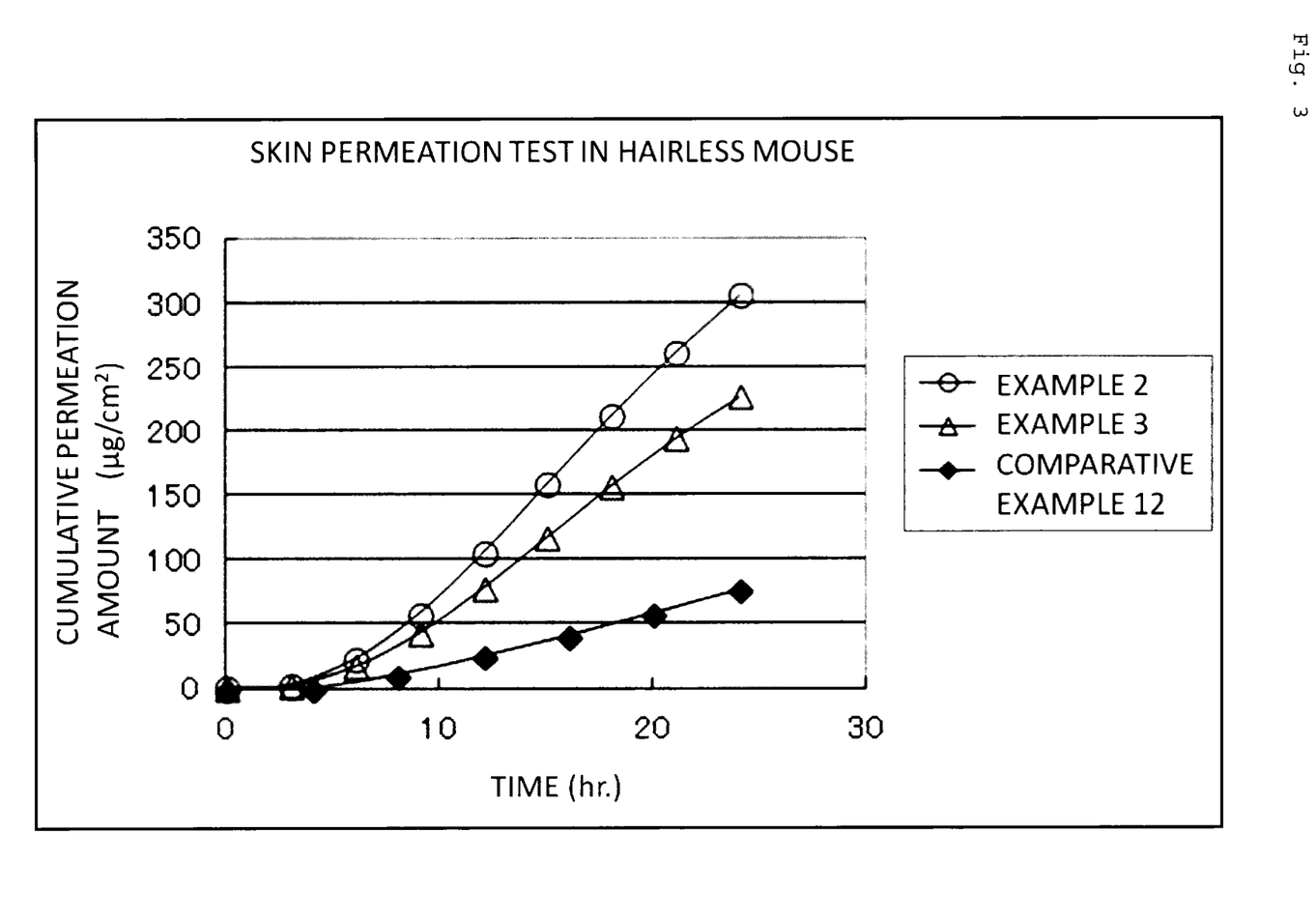
FIG. 3 is a graph showing the time-dependent changes of cumulative skin permeation amounts of diclofenac in the skins of hairless mice on which diclofenac sodium-containing patches are attached.

Also, as for the patch of Example 2 and a 1% diclofenac-containing patch that was commercially available (Comparative Example 12), the skin permeabilities of diclofenac sodium in mouse skins were evaluated. The obtained results are shown in FIG. 3. In addition, as for the patches of Example 2 and Comparative Example 12, the skin permeabilities of diclofenac sodium in human skins were evaluated. The obtained results are shown in FIG. 4.

Figure 4:
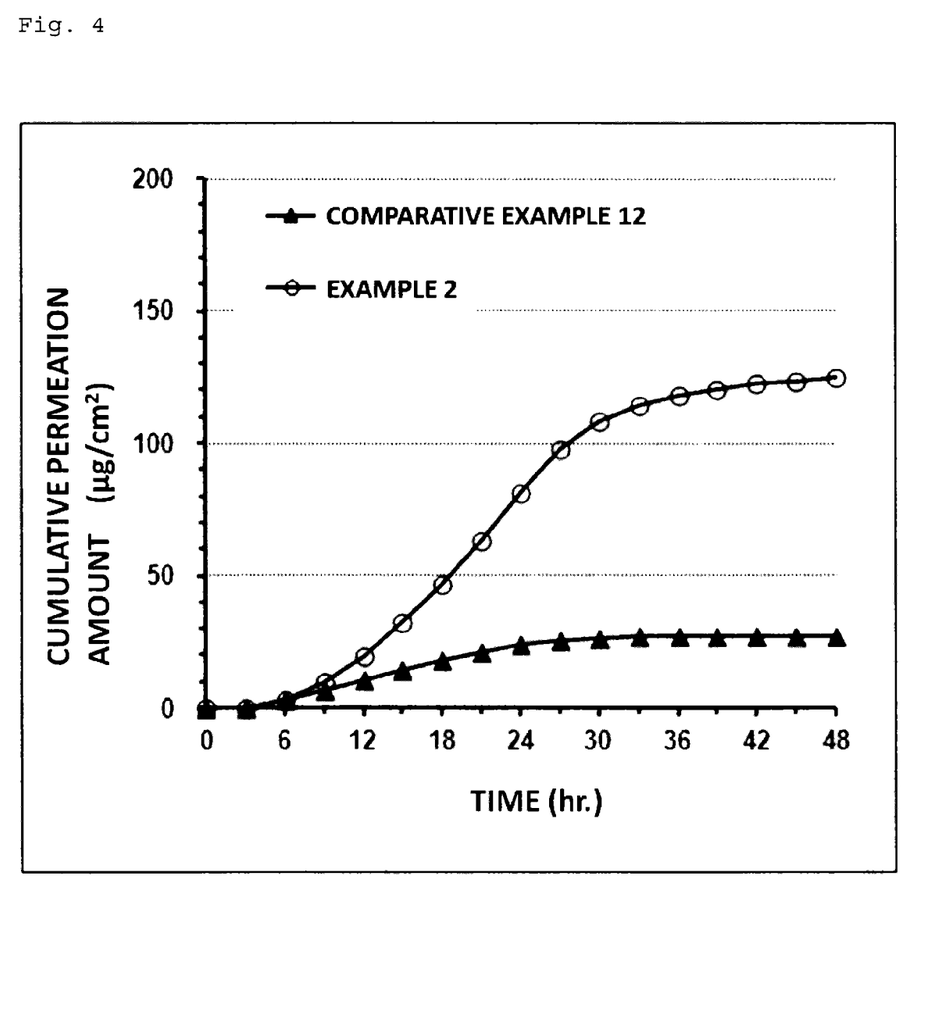
FIG. 4 is a graph showing the time-dependent changes of cumulative skin permeation amounts of diclofenac in the skins of humans on which diclofenac sodium-containing patches are attached.

As is evident from the results shown in FIGS. 3 and 4, the patches of the present invention allowed large amounts of diclofenac per unit area to permeate through either of mouse and human skins as compared with the patches comprising no adhesive layer according to the present invention.

Next, based on the results from the evaluation of the human skin permeability as shown in FIG. 4, pharmakinetics in humans were predicted in cases where one to three sheets of the patch of Example 2 (area: 140 cm$^2$) were attached to the skin by performing convolution from the results of the permeation test with the use of the human skins. Also, in the cases of oral agents comprising diclofenac sodium [VOLTAREN (registered trademark) tablet with a content of 25 mg-three doses daily and VOLTAREN (registered trademark) SR capsule with a content of 37.5 mg-two doses daily], the prediction was made based on the pharmakinetics data of the respective package inserts. The obtained results are shown in FIGS. 5 to 7.

Figure 5:
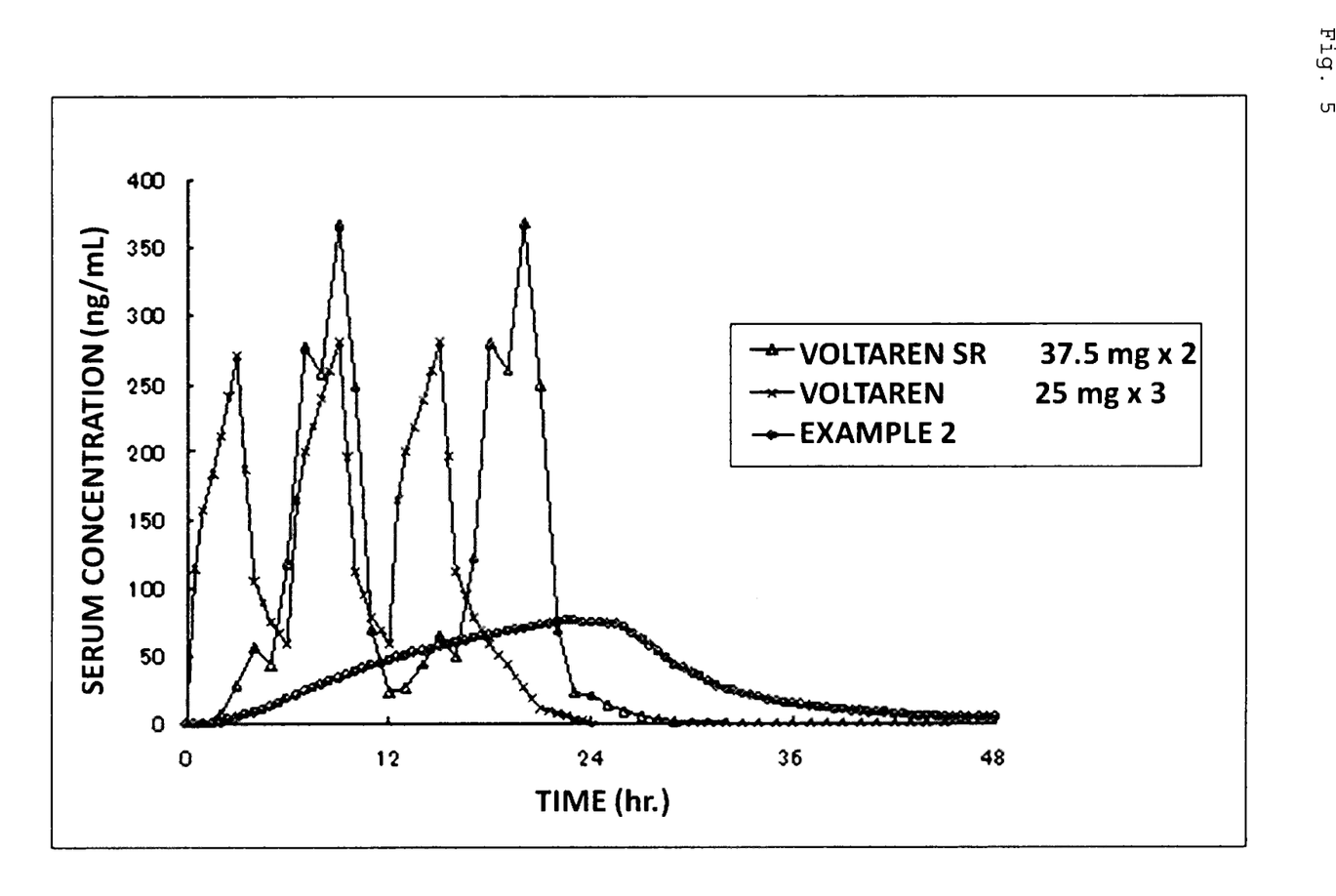
FIG. 5 is a graph showing the results that were predicted using a simulation software with respect to the time-dependent change of blood concentration when one sheet of a patch according to the present invention (Example 2) was attached to the skin, and the time-dependent changes of blood concentrations when diclofenac sodium-containing oral agents [VOLTAREN (registered trademark) tablet and VOLTAREN (registered trademark) SR capsule] were orally administered.
Figure 6:
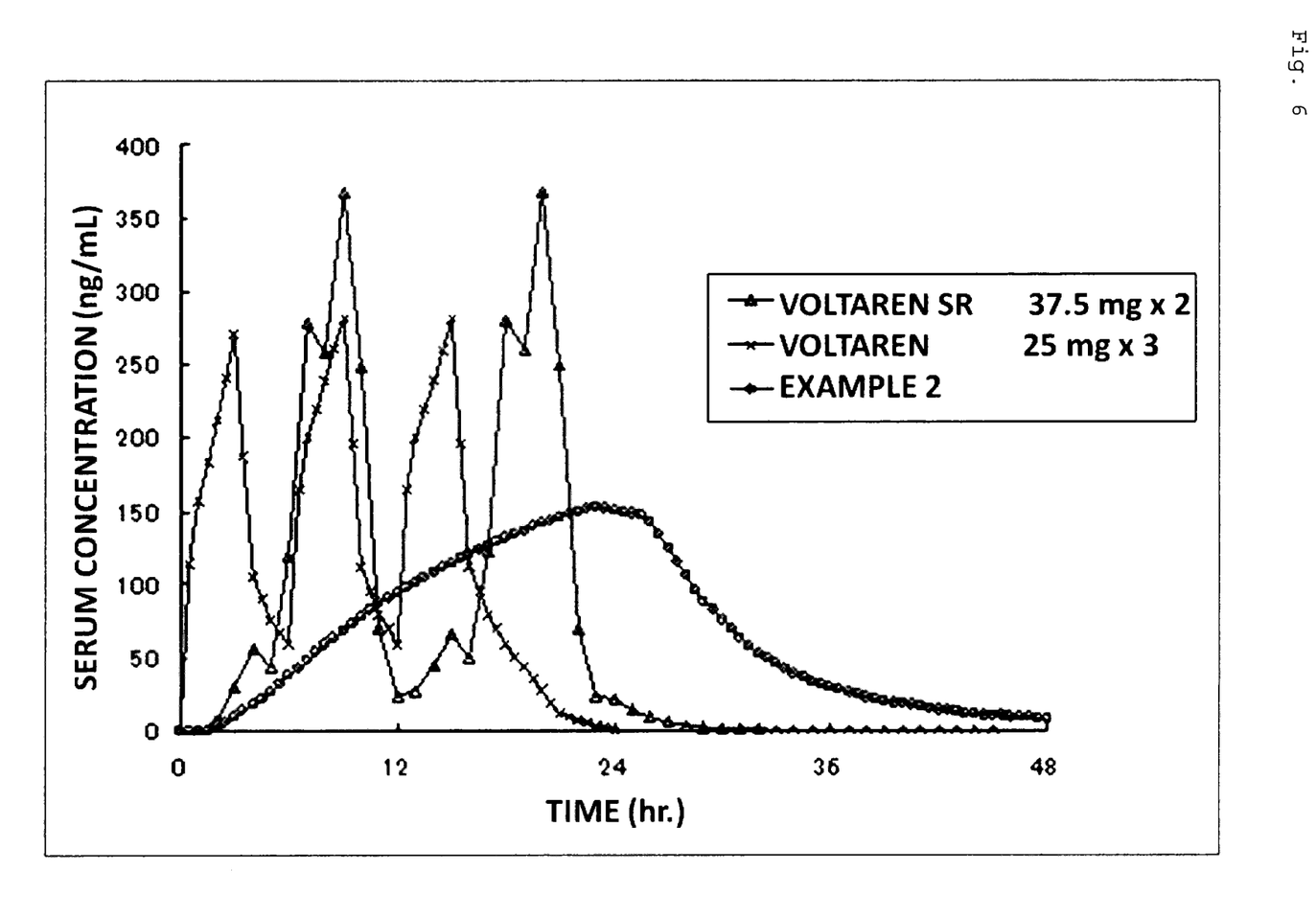
FIG. 6 is a graph showing the results that were predicted using a simulation software with respect to the time-dependent change of blood concentration when two sheets of the patch according to the present invention (Example 2) were attached to the skin, and the time-dependent changes of blood concentrations when diclofenac sodium-containing oral agents [VOLTAREN (registered trademark) tablet or VOLTAREN (registered trademark) SR capsule] were orally administered.
Figure 7:
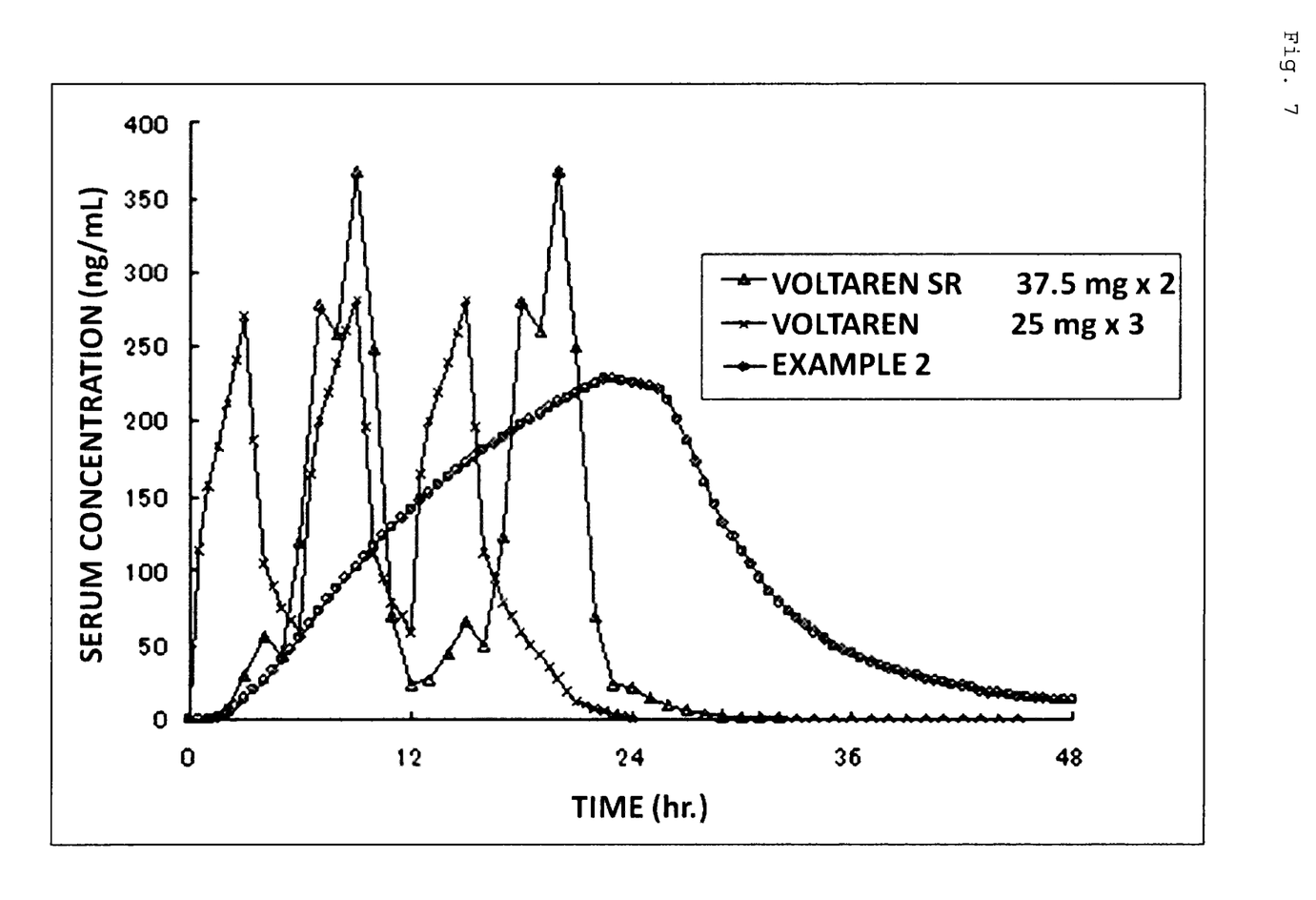
FIG. 7 is a graph showing the results that were predicted using a simulation software with respect to the time-dependent change of blood concentration when three sheets of the patch according to the present invention (Example 2) were attached to the skin, and the time-dependent changes of blood concentrations when diclofenac sodium-containing oral agents [VOLTAREN (registered trademark) tablet or VOLTAREN (registered trademark) SR capsule] were orally administered.

As is evident from the results shown FIGS. 5 to 7, when two to three sheets of the patch of the present invention (Example 2, area: 140 cm$^2$) were attached, areas under the blood concentration-time curve (AUC) at almost the same levels as those for the oral agents could be obtained.

Examples 5-9 and Comparative Examples 9-11

First, the components listed in Table 4 were weighted out so that they were to be respectively predetermined mass percentages, further mixed after the addition of toluene, and dissolved or dispersed to obtain adhesive layer compositions. Next, they were applied onto one-side surfaces of release liners, and after drying, surfaces that were opposite to the release liners were covered with support layers and pressure-adhered, whereby patches were obtained. Note that the value in a parenthesis of table 4 represents the mass part of each component (dimethyl sulfoxide, citric acid or ammonium chloride) when diclofenac sodium in the adhesive layer of each of the respective examples and comparative examples was made one mass part.

TABLE 4

|  | Example 5 | Example 6 | Example 7 | Example 8 | Example 9 | Comparative Example 9 | Comparative Example 10 | Comparative Example 11 |
|---|---|---|---|---|---|---|---|---|
| Diclofenac sodium | 5(1) | 5(1) | 5(1) | 5(1) | 5(1) | 3(1) | 5(1) | 5(1) |
| Dimethyl sulfoxide | 5(1.00) | 5(1.00) | 10(2.00) | 10(2.00) | 15(3.00) | — | 1(0.20) | 10(2.00) |
| Citric acid | 0.9(0.18) | 2.11(0.42) | 2.11(0.42) | 0.91(0.18) | 0.91(0.18) | — | 0.9(0.18) | 0.3(0.06) |
| Ammonium chloride | — | — | — | — | — | 1(0.33) | — | — |
| Styrene-isoprene-styrene block copolymer | 15 | 15 | 15 | 15 | 15 | 15 | 15 | 15 |
| Polyisobutylene | 5 | 5 | 5 | 5 | 5 | 5 | 5 | 5 |
| Liquid paraffin | 34.1 | 32.89 | 27.89 | 29.09 | 24.09 | 41 | 38.09 | 29.7 |
| Alicyclic saturated hydrocarbon resin | 15 | 15 | 15 | 15 | 15 | 10 | 15 | 15 |
| Hydrogenated rosin ester | 15 | 15 | 15 | 15 | 15 | 20 | 15 | 15 |
| Oleic acid | 5 | 5 | 5 | 5 | 5 | 3 | 5 | 5 |
| Polyethylene glycol | — | — | — | — | — | 2 | — | — |

Figure 8:
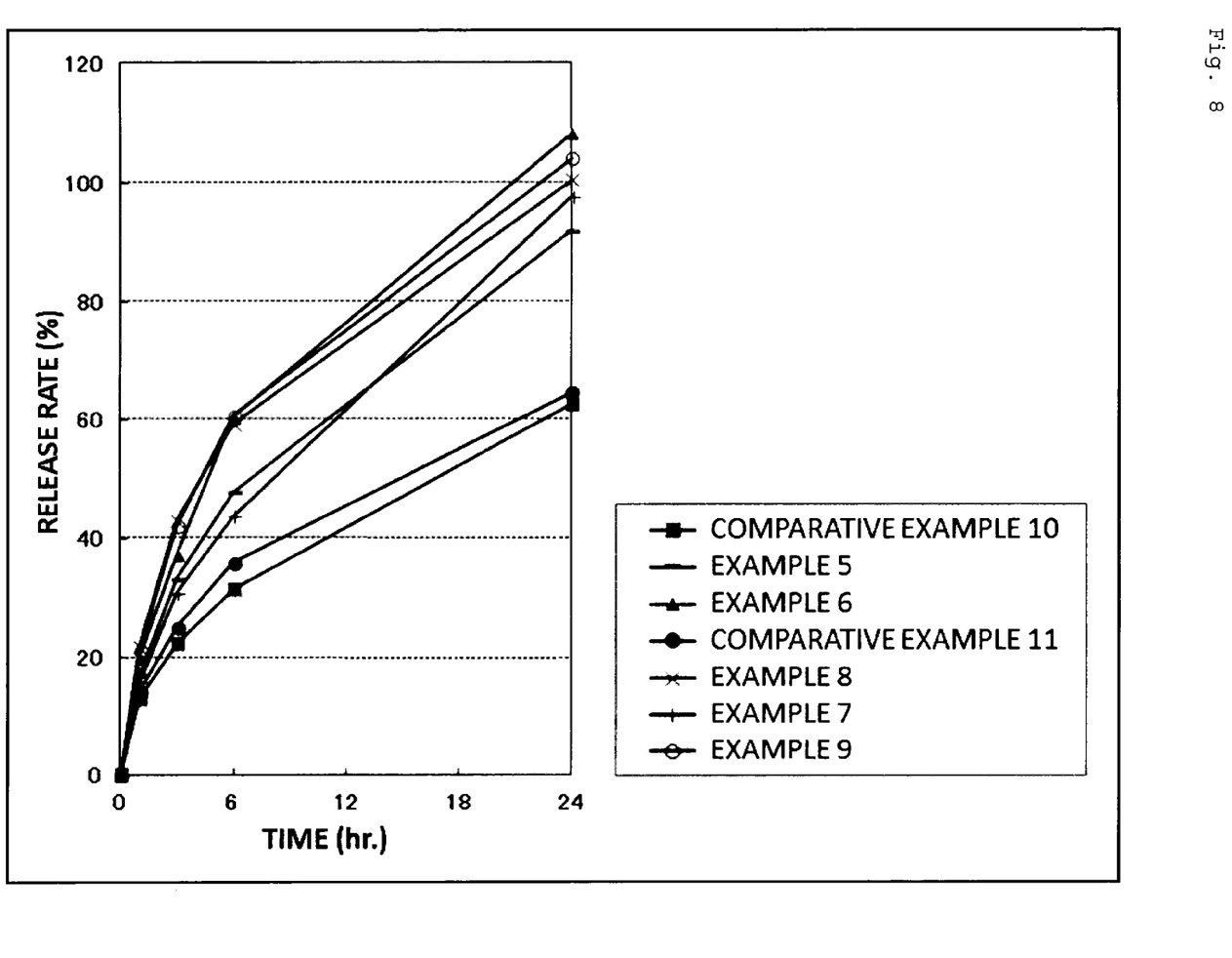
FIG. 8 is a graph showing the results of water releasability with respect to diclofenac sodium-containing patches (Examples 5-9 and Comparative Examples 10 and 11) having been analyzed.

Further, as for the patches of Examples 5-9 and Comparative Examples 10 and 11, water releasability was evaluated. The obtained results are shown in FIG. 8. As is evident from the results shown in FIG. 8, the patches of the present invention (Examples 5-9) were also superior in the water releasability (drug releasability) to the patches that did not comprise the adhesive layers of the present invention (Comparative Examples 10 and 11): specifically, the patches of the present invention are those wherein the adhesive layer comprises diclofenac sodium, dimethyl sulfoxide, and citric acid; a mass ratio between the diclofenac sodium and the citric acid is 1:0.15 to 1:0.45; and a mass ratio between the diclofenac sodium and the dimethyl sulfoxide (mass of diclofenac sodium:mass of dimethyl sulfoxide) is 1:0.75 to 1:3.

Furthermore, as for the patches of Examples 5-9 and Comparative Examples 10 and 11, adhesive forces were evaluated. The obtained results are shown in Table 5. Note that the amount of citric acid or dimethyl sulfoxide (DMSO) represents the mass part of each component when diclofenac sodium in the adhesive layer of each of the examples and comparative examples was made one mass part.

TABLE 5

| | | Citric acid | | |
|---|---|---|---|---|
| | | 0.06 | 0.13 | 0.42 |
| DMSO | 0.2 | — | 300.42 gf (Comparative Example 10) | — |
| | 1 | — | 276.82 gf (Example 5) | 219.22 gf (Example 6) |
| | 2 | 224.2 gf (Comparative Example 11) | 266.19 gf (Example 8) | 211.49 gf (Example 7) |
| | 3 | — | 35.73 gf (Example 9) | — |

As is evident from the results shown in Table 5, the patches (Examples 5-8 and Comparative Examples 10 and 11), each of which comprises an adhesive layer, the adhesive layer comprising diclofenac sodium, dimethyl sulfoxide, and citric acid wherein a mass ratio between the diclofenac sodium and the dimethyl sulfoxide (mass of diclofenac sodium:mass of dimethyl sulfoxide) is 1:0.2 to 1:2 are provided with strong adhesive force. By contrast, the patch (Example 9) comprising an adhesive layer which comprises 3 mass parts, i.e., exceeding 2 mass parts, of the dimethyl sulfoxide relative to 1 mass part of the diclofenac sodium is insufficient from the standpoint of adhesive force.

INDUSTRIAL APPLICABILITY

As described above, according to the present invention, it is possible to provide a patch wherein the crystallization of diclofenac and diclofenac sodium is suppressed, the skin irritation is less and the skin permeability of diclofenac is excellent.

Accordingly, since the patch of the present invention can suppress the crystallization of diclofenac and diclofenac sodium, can stably comprise diclofenac at a high concentration (3% by mass or greater relative to the total mass of the adhesive layer) and can further exert the excellent skin permeability of diclofenac, it is useful not only as a drug that is intended for local analgesic, anti-inflammatory action but also as a drug that is intended for systemic analgesic, anti-inflammatory action.

The invention claimed is:

1. A patch comprising a support layer and an adhesive layer, wherein the adhesive layer comprises diclofenac sodium, dimethyl sulfoxide, and citric acid; a mass ratio between the diclofenac sodium and the citric acid (mass of diclofenac sodium:mass of citric acid) is 1:0.15 to 1:0.45; and a mass ratio between the diclofenac sodium and the dimethyl sulfoxide (mass of diclofenac sodium:mass of dimethyl sulfoxide) is 1:0.75 to 1:2.

2. The patch according to claim 1, wherein the adhesive layer further comprises oleic acid.

3. The patch according to claim 2, wherein a content of the oleic acid is 1 to 10% by mass relative to the total mass of the adhesive layer.

4. The patch according to claim 1, wherein a total content of the citric acid and the dimethyl sulfoxide is 1 to 15% by mass relative to the total mass of the adhesive layer.

5. The patch according to claim 1, wherein a content of the diclofenac sodium is 2 to 10% by mass relative the total mass of the adhesive layer; and a content of the dimethyl sulfoxide is 3 to 10% by mass relative to the total mass of the adhesive layer.

6. The patch according to claim 1, wherein an adhesive comprised in the adhesive layer is a styrene-isoprene-styrene block copolymers and/or polyisobutyrene.

7. The patch according to claim 1, wherein the adhesive layer further comprises at least one compound selected from the group consisting of an alicyclic saturated hydrocarbon resin, a hydrogenated rosin ester, and a terpene resin.

8. The patch according to claim 1, wherein the adhesive layer further comprises at least one compound selected from the group consisting of liquid paraffin and a liquid rubber.

* * * * *